United States Patent [19]

Kulkarni et al.

[11] Patent Number: 5,573,754

[45] Date of Patent: Nov. 12, 1996

[54] PHOTOPROTECTIVE COMPOSITIONS

[75] Inventors: Rupali A. Kulkarni, Huntington; George E. Deckner, Trumbull, both of Conn.

[73] Assignee: Richardson-Vicks Inc., Shelton, Conn.

[21] Appl. No.: 174,590

[22] Filed: Dec. 28, 1993

Related U.S. Application Data

[63] Continuation of Ser. No. 23,852, Feb. 26, 1993, abandoned, which is a continuation of Ser. No. 732,954, Jul. 19, 1991, abandoned, which is a continuation of Ser. No. 445,313, Dec. 4, 1989, abandoned.

[51] Int. Cl.$^6$ ................................ A61K 7/42; A61K 7/40
[52] U.S. Cl. ................................ 424/59; 424/60
[58] Field of Search .......................... 424/59, 60

[56] References Cited

U.S. PATENT DOCUMENTS

| | | | |
|---|---|---|---|
| 4,603,046 | 7/1986 | Georgalas et al. | 514/847 |
| 4,737,360 | 4/1988 | Allen et al. | 424/60 |
| 4,742,066 | 5/1988 | Deckner et al. | 514/917 |
| 4,743,442 | 5/1988 | Raaf et al. | 424/59 |
| 4,833,259 | 5/1989 | Erlemann et al. | 424/60 |
| 4,847,069 | 7/1989 | Bissett et al. | 424/47 |
| 4,847,071 | 7/1989 | Bissett et al. | 424/59 |
| 4,847,072 | 7/1989 | Bissett et al. | 424/59 |
| 4,847,247 | 7/1989 | Deckner et al. | 514/311 |
| 4,847,267 | 7/1989 | Deckner et al. | 514/311 |
| 4,869,897 | 9/1989 | Chatterjee et al. | 424/47 |
| 4,919,934 | 4/1990 | Deckner et al. | 424/401 |

OTHER PUBLICATIONS

*The Merck Index*, 10th Ed. (published 1983 by Merck & Company, Inc, Rahway, NJ) No.'s 242 ("Allantoin"), 2910 (Dexpanthenol), 9832 (Vitamin E) and 9833 (Vitamin E acetate).

*Primary Examiner*—Shelley A. Dodson
*Attorney, Agent, or Firm*—Kim W. Zerby; Anthony D. Sabatelli; David K. Dabbiere

[57] ABSTRACT

High SPF value (about 8 or greater) sunscreen compositions having improved photoprotective properties by non-sunscreen mechanism. These compositions comprise allantoin; pantothenol; Vitamin E, its pharmaceutically-acceptable esters, or mixtures thereof; one or more sunscreen agents; and carrier material.

14 Claims, No Drawings

PHOTOPROTECTIVE COMPOSITIONS

This is a continuation of application Ser. No. 08/023,852, filed on Feb. 26, 1993, now abandoned, which is a continuation of application Ser. No. 732,954, filed on Jul. 19, 1991, which is a continuation of application Ser. No. 445,313 filed Dec. 4, 1989, now abandoned.

TECHNICAL FIELD

This invention relates to improved topical compositions having enhanced photoprotective properties useful for protecting the skin from the harmful effects of ultraviolet irradiation, such as sunburn and sun-induced premature aging of the skin.

BACKGROUND OF THE INVENTION

The damaging effects of sunlight on skin are well documented. Contrary to what most people believe, it is not necessary that one sunbathe to suffer the ill-effects of excessive UV exposure. In fact, a lot of damage can be done just by routine day-to-day activities in the sunlight. Some scientists estimate that over 70 percent of the damage the sun inflicts on the average person's skin over a lifetime is the result of simply being outdoors or even sitting by a window.

The major short term hazard of prolonged exposure to sunlight is erythema (i.e., sunburn). The 290 to 320 nanometer wavelength ultraviolet radiation range, designated as the "UVB" wavelength range, tends to be the primary cause of erythema. The 320 to 400 nanometer wavelength ultraviolet radiation range, designated as the "UVA" wavelength range, also produces erythema.

In addition to the short term hazard or erythema, there are also long term hazards associated with UV radiation exposure. One of these long term hazards is malignant changes in the skin surface. Numerous epidemiologic studies demonstrate a strong relationship between sunlight exposure and human skin cancer.

Another long term hazard of ultraviolet radiation is premature aging of the skin. This condition is characterized by wrinkling and yellowing of the skin, along with other physical changes such as cracking, telangiectasis (spider vessels), solar keratoses (growths), ecchymoses (subcutaneous hemorrhagic lesions), and loss of elasticity (sagging). The adverse effects associated with exposure to UVA and UVB wavelength radiation are more fully discussed in DeSimone, "Sunscreen and Suntan Products", *Handbook of Nonprescription Drugs*, 8th Ed., Chapter 26, pp. 533–546 (American Pharmaceutical Association, Washington, D.C.; 1986); Grove and Forbes, "A Method for Evaluating the Photoprotection Action of Sunscreen Agents Against UV-A Radiation", *International Journal of Cosmetic Science*, 4, pp. 15–24 (1982); and U.S. Pat. No. 4,387,089, DePolo, issued Jun. 7, 1983; the disclosures of all of which are incorporated herein by reference in their entirety. Hence, although the immediate effects of ultraviolet radiation may be cosmetically and socially gratifying, the long-term hazards are cumulative and potentially serious.

The fact that these effects are taken seriously by the general public is suggested by considering the sun protection products market. This market has grown considerably in recent years and many new products are introduced each year. What used to be looked upon as a seasonal business is no longer. Sun protection compounds are now included in a diversity of personal care products, particularly cosmetic-type products which are worn on a daily basis.

The most common agents for sun protection are sunscreens. These agents exert their effect through chemical means, i.e., they absorb ultraviolet radiation so that it cannot penetrate the skin. More and more consumers are interested in using products which contain sunscreen agents, but are both more sun protective and more cosmetically appealing.

U.S. Pat. Nos. 4,847,267, issued Jul. 11, 1989 and 4,742,066, issued May 3, 1988, both to Deckner et al., relate to skin treatment compositions which inhibit generation of free radicals in the skin. Optional components for use in these compositions include skin conditioning agents (including allantoin and panthenol), ultraviolet absorbing agents, and vitamins such as Vitamin E.

U.S. Pat. No. 4,833,259, issued May 23, 1989, to Erlemann et al., describes sunscreen agents which are esters of p-methoxycinnamic acid with d,l-alpha-tocopherol, pantolactone or panthenol. Allantoin, Vitamin E acetate and panthenol are optional components exemplified therein.

U.S. Pat. No. 4,743,442, issued May 10, 1988, to Raaf et al., describes skin care compositions containing mineral salts. Optional components include substances for absorbing UV-radiation, Vitamin E, panthenol, and allantoin.

U.S. Pat. No. 4,737,360, issued Apr. 12, 1988, to Allen et al., describes skin care compositions comprising a pollen extract and non-animal and non-mineral oils. Optional components are said to include UV screens. Example 4 describes a deep cleaning milk containing tocopherol, allantoin, and DL-panthanol.

U.S. Pat. No. 4,603,046, issued Jul. 29, 1986, to Georgalas et al., relates to skin treatment compositions, such as sunscreen compositions, which include a tri(dihydroxyalkyl)rutoside as a UV-A absorber and moisturizer. Optional components for use in these compositions include skin conditioning agents (including allantoin and panthenol), ultraviolet absorbing agents, and vitamins such as Vitamin E.

It is an object of the present invention to provide topical compositions which will prevent acute (erythema) and chronic (photoaging) effects of exposure to the sun. An object is also to increase the photoprotectiveness of highly photoprotective sunscreen compositions via a non-sunscreen mechanism. It is a further object to provide cosmetically-acceptable compositions which further enhance the sun protective benefit provided by sunscreen actives and, if desired, still permit tanning of the skin to occur. An additional object is to provide an inexpensive and safe way to increase the photoprotectiveness of highly photoprotective sunscreen compositions and, if desired, thereby use lower concentrations of sunscreen agents. Finally, an object is to provide sunscreen compositions which have better consumer acceptance and/or are more soothing to the skin.

These and other objects of the present invention will become readily apparent from the detailed description which follows.

All percentages and ratios used herein are by weight, and all measurements made at 25° C., unless otherwise specified.

SUMMARY OF THE INVENTION

The present invention relates to sunscreen compositions having enhanced photoprotective properties. These compositions comprise:

(a) from about 0.1% to about 2% allantoin;

(b) from about 0.1% to about 5% pantothenol;

(c) from about 0.1% to about 5% Vitamin E, its pharmaceutically-acceptable esters, or mixtures thereof;

(d) from about 1% to about 30% of one or more sunscreen agents; and (e) from about 60% to about 99% of a pharmaceutically-acceptable sunscreen carrier material;

and wherein further said sunscreen compositions have a Sun Protection Factor ("SPF") value of about 8 or greater.

The present invention further relates to methods for providing photoprotection comprising topically applying to a human or lower animal in need of photoprotection a safe and photoprotectively effective amount of a sunscreen composition according to the present invention.

DETAILED DESCRIPTION OF THE INVENTION

I. Sunscreen Compositions

The present invention relates to improved sunscreen compositions having enhanced photoprotective properties. These sunscreen compositions have high Sun Protection Factor (herein "SPF") values of about 8 or greater. Said compositions comprise: (a) allantoin; (b) pantothenol (preferably d-pantothenol and DL-panthenol); (c) Vitamin E, pharmaceutically-acceptable esters thereof, or mixtures thereof (preferably Vitamin E acetate, especially the d-alpha form thereof); (d) one or more sunscreen agents; and (e) pharmaceutically-acceptable sunscreen carrier material.

It has surprisingly been discovered that high SPF value sunscreen compositions according to the present invention demonstrate a substantial increase in SPF in vivo, whereas in vitro this enhancement in SPF is not observed. Thus, there is an unexpected SPF boost obtained which is not attributable to a sunscreen mechanism for these compositions. Therefore, compositions of the present invention provides substantially greater photoprotectiveness than otherwise expected from the sunscreen agents utilized in the compositions. The higher the SPF of these compositions, the greater this non-sunscreen boost in SPF appears to be. Below SPF of about 8, little or no boost in SPF is observable.

The term "pharmaceutically-acceptable", as used herein, means that the components present in the compositions of the present invention are compatible and suitable for topical administration to a human or lower animal. The term "compatible", as used herein, means that the components of the sunscreen compositions are capable of being commingled with each other in a manner such that there is no interaction which would substantially reduce the photoprotective efficacy of the compositions, or the effectiveness of the sunscreen agents, under ordinary use situations. Pharmaceutically-acceptable components for use herein must, of course, be of sufficiently high purity and sufficiently low toxicity to render them suitable for topical administration to the human or lower animal using said compositions.

The essential and optional components for use in the compositions of the present invention, and the amounts to be utilized, are described in detail hereinafter.

(a) Allantoin

The sunscreen compositions of the present invention comprise allantoin. This component is described in detail in *The Merck Index,* 10th Ed. (published 1983 by Merck & Company, Inc., Rahway, N.J.) No. 242, "Allantoin", the disclosures contained therein being incorporated by reference herein in their entirety. This material is commercially available from Shultz Corporation, Germany/Aceto Chemical Distributor, ICI Americas and Sutton Laboratories, Inc.

The compositions of the present invention typically comprise from about 0.1% to about 2% allantoin, preferably from about 0.1% to about 1%, and more preferably from about 0.1% to about 0.5%.

(b) Pantothenol

The sunscreen compositions of the present invention further comprise pantothenol, preferably the d-form, either by itself or as the dl-form mixture (herein "DL-panthenol"). This material is described in detail in *The Merck Index,* 10th Ed. (published 1983 by Merck & Company, Inc., Rahway, N.J.) No. 2910, "Dexpanthenol", the disclosures contained therein being incorporated herein by reference in their entirety. It is also possible to utilize this component in other forms, for example as liposomes. DL-Panthenol (cosmetic grade) is commercially available from Hoffman-LaRoche, Inc. and Koffolk.

The compositions of the present invention typically comprise from about 0.1% to about 5% pantothenol (preferably d-pantothenol or DL-panthenol), preferably from about 0.1% to about 3%, and more preferably from about 0.1% to about 1%.

(c) Vitamin E or pharmaceutically-acceptable esters of Vitamin E

The sunscreen compositions of the present invention also comprise Vitamin E (also known as "alpha-tocopherol"), pharmaceutically-acceptable esters thereof (preferably Vitamin E acetate, especially the d-form and dl-form), or mixtures of Vitamin E and esters thereof (e.g., Vitamin E and Vitamin E acetate). These compounds are more fully described in *The Merck Index,* 10th Ed. (published 1983 by Merck & Company, Inc., Rahway, N.J.) No. 9832, "Vitamin E", and No. 9833, "Vitamin E acetate", the disclosures contained therein being incorporated herein by reference in their entirety. It is possible to utilize this component in other forms, for example as liposomes or microcapsules. Vitamin E acetate is commercially available from Hoffman-LaRoche, Inc.

The compositions of the present invention typically comprise from about 0.1% to about 5% Vitamin E, its pharmaceutically-acceptable ester, or mixtures thereof (preferably Vitamin E acetate), preferably from about 0.1% to about 3%, and more preferably from about 0.1% to about 1%.

(d) Sunscreen Agents

The compositions of the present invention also comprise one or more sunscreen agents. A wide variety of conventional sunscreening agents are suitable for use in the present invention. Segarin, et al., at Chapter VIII, pp. 189 et seq., of *Cosmetics Science and Technology,* disclose numerous suitable agents. Specific suitable sunscreening agents include, for example: p-Aminobenzoic acid, its salts and its derivatives (ethyl, isobutyl, glyceryl esters; p-dimethylaminobenzoic acid); Anthranilates (i.e., o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, phenyl cinnamonitrile, butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl ); Diazoles (2-acetyl -3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzene, Sulisbenzone, Dioxybenzone, Benzoresorcinol, 2,2',4,4'-Tetrahydroxybenzophenone, 2,2'-Dihydroxy-4,4'-dimethoxybenzophenone, Octabenzone); 4-Isopropyldibenzoylmethane; Butylmethoxydibenzoylmethane; Etocrylene; Octocrylene; titanium dioxide; and 4-isopropyl-di-benzoylmethane; and mixtures thereof.

Of these, 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)]aminobenzoate, 2-ethylhexy12-cyano-3,3-diphenylacrylate, octocrylene, titanium dioxide, 2-ethylhexysalicylate, glyceryl p-aminobenzoate, 3,3,,5-trimethylcyclohexysalicylate, methylanthranilate, menthyl anthranilate, p-dimethyl-aminobenzoic acid or aminobenzoate, 2-ethylhexyl p-dimethylamino-benzoate, 2-phenylbenzimidazole-5-sulfonic acid, 2-(p-dimethylaminophenyl)-5-sulfonicbenzoxazoic acid and mixtures of these compounds, are particularly useful.

Preferred sunscreens useful in the compositions of the present invention are 2-ethylhexyl p-methoxycinnamate, butyl methoxydibenzoylmethane, 2-hydroxy-4-methoxybenzophenone, octyldimethyl p-aminobenzoic acid, 2,2'-dihydroxy-4-methoxybenzophenone, octocrylene, menthyl anthranilate, titanium dioxide, and ethyl hexyl salicylate, and mixtures thereof.

Also particularly useful in the present invention are sun screens such as those disclosed in European Patent Application Publication No. 251,398, published Jan. 7, 1988, and in European Patent Application Publication No. 255,157, published Feb. 3, 1988, the disclosures of both being incorporated herein by reference in their entirety. The sunscreening agents disclosed therein have, in a single molecule, two distinct chromophore moieties which exhibit different ultraviolet radiation absorption spectra. One of the chromophore moieties absorbs predominantly in the UVB radiation range and the other absorbs strongly in the UVA radiation range. These sunscreening agents provide higher efficacy, broader UV absorption, lower skin penetration and longer lasting efficacy relative to conventional sunscreens.

Preferred members of this class of sunscreening agents are selected from the group consisting of 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N(2-ethylhexyl) methylaminobenzoic acid ester with 4-hydroxydibenzoylmethane; 4-N,N-(2-ethylhexyl)methylaminobenzoic acid ester of 2-hydroxy-4-(2-hydroxyethoxy)benzophenone; 4-N,N-(2-ethylhexyl) methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)4-aminobenzoic acid ester of 4-(2-hydroxyethoxy)dibenzoylmethane; and mixtures thereof.

A safe and photoprotectively effective amount of sunscreen may be used in the sunscreen compositions of the present invention. By "safe and photoprotectively" is meant an amount sufficient to provide photoprotection when the composition is applied not so much as to cause any side effects or skin reactions. Generally from about 1% to about 30%, preferably from about 2% to about 20%, of the composition may comprise a sunscreening agent. Exact amounts will vary depending upon the sunscreen chosen and the desired SPF.

SPF is a commonly used measure of photoprotection of a sunscreen against erythema. This number is derived from another parameter, the minimal erythemal dose ("MED"). MED is defined as the "least exposure dose at a specified wavelength that will elicit a delayed erythema response." (DeSimone, "Sunscreen and Suntan Products", *Handbook of Nonprescription Drugs*, 8th Ed., p. 535 (American Pharmaceutical Association, Washington, D.C.; 1986), and the references cited therein all incorporated herein by reference in their entirety.) The MED indicates the amount of energy reaching the skin and the responsiveness of the skin to the radiation. The SPF of a particular photoprotector is obtained by dividing the MED of protected skin by the MED of unprotected skin. SPF and MED are more fully discussed in DeSimone, "Sunscreen and Suntan Products" and the references cited therein which are incorporated hereinbefore by reference in their entirety.

The higher the SPF, the more effective the agent in preventing sunburn. The SPF value tells how many times longer a person can stay in the sun with use of the sunscreen (compared to a person with unprotected skin) before that person will experience 1 MED. For example, utilizing a sunscreen with an SPF of 6 will allow an individual to stay in the sun six times longer before receiving 1 MED. As the SPF value of a sunscreen increases, less chance exists for development of tanning of the skin. Commercially available sunscreening products have SPF values ranging from about 2 to about 55. For purposes of the present invention of providing enhanced photoprotective effect, the compositions of the present invention are those having SPF values of about 8 or greater, preferably about 15 or greater, and more preferably about 20 or greater.

(e) Pharmaceutically-Acceptable Sunscreen Carrier Materials

The present invention further comprises pharmaceutically-acceptable sunscreen carrier materials selected as appropriate for the form and aesthetic characteristics desired for the compositions of the present invention being formulated. Suitable carrier materials useful for sunscreen compositions as described herein are well known in the art, and their selection are readily made by one skilled in the art. Some of the many materials which may be selected as suitable as carrier materials are described in detail as follows.

(1) Emulsifier

The compositions of the present invention preferably comprise at least one emulsifier. Preferred is the use of alkyl substituted acrylic acid copolymers comprising polymers of a monomeric mixture containing 95.9 to 98.8 weight percent of an olefinically unsaturated carboxylic monomer selected from the group consisting of acrylic, methacrylic and ethacrylic acids, about 1 to about 3.5 weight percent of an acrylate ester of the formula

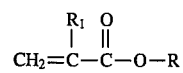

wherein R is hydrogen or an alkyl radical containing 10 to 30 carbon atoms and $R_1$ is hydrogen, methyl or ethyl, and 0.1 to 0.6 weight percent of a polymerizable cross-linking polyalkenyl polyether of a polyhydric alcohol containing more than one alkenyl ether group per molecule wherein the parent polyhydric alcohol contains at least 3 carbon atoms and at least 3 hydroxyl groups.

Preferably, these polymers contain from about 96 to about 97.9 weight percent of acrylic acid and from about 2.5 to about 3.5 weight percent of acrylic esters wherein the alkyl group contains 12 to 22 carbon atoms, and $R_1$ is methyl, most preferably the acrylate ester is stearyl methacrylate. Preferably, the amount of crosslinking monomer is from about 0.2 to 0.4 weight percent. The preferred crosslinking monomers are allyl pentaerythritol, trimethylolpropane diallylether or allyl sucrose. These polymers are fully described in U.S. Pat. No. 4,509,949, Huang et al., issued Apr. 5, 1985.

The carboxylic monomers useful in the production of such polymers are the olefinically-unsaturated carboxylic acids containing at least one activated carbon-to-carbon olefinic double bond, and at least one carboxyl group.

The preferred carboxylic monomers are the acrylic acids having the general structure

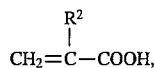

$$CH_2=\overset{R^2}{\underset{|}{C}}-COOH,$$

wherein $R^2$ is a substituent selected from the class consisting of hydrogen, halogen, and the cyanogen (—C≡N) groups, monovalent alkyl radicals, monovalent alkaryl radicals and monovalent cycloaliphatic radicals. Of this class, acrylic, methacrylic, and ethacrylic acid are most preferred. Another useful carboxylic monomer is maleic anhydride or the acid. The amount of acid used will be from about 95.5 to about 98.9 weight percent of the total monomers used. More preferably the range will be from about 96 to about 97.9 weight percent.

The polymers are crosslinked with a polyfunctional vinylidene monomer containing at least 2 terminal $CH_2<$ groups, including for example, butadiene, isoprene, divinyl benzene, divinyl naphthlene, allyl acrylates, and the like. Particularly useful crosslinking monomers for use in preparing the copolymers are polyalkenyl polyethers having more than one alkenyl ether grouping per molecule. The most useful possess alkenyl groups in which an olefinic double bond is present attached to a terminal methylene grouping, $CH_2=C<$. Most preferred from this class are Carbomer 1342 and/or Carbomer 934 (available as Carbopol 1342 and/or Carbopol 934, and Carbopol 954 and/or Carbopol 1352, from B.F. Goodrich).

Also useful are TEA stearate salts, alkali neutralized mono- and di-alkyl phosphates including diethanolamine mono- and di-cetyl phosphate (available from Givaudan as Amphisol) and hydroxy cetyl phosphate (available from Henkel as Forlanit E).

The emulsifiers used in the present invention should be dispersable (but not soluble) in water.

Emulsifiers preferably comprise in total from about 0.01% to about 5%, more preferably from about 0.05% to about 3%, and most preferably from about 0.05% to about 1%, of the compositions of the present invention.

(2) Wax Component

Another optional component of the compositions herein is a wax component having an HLB of from about 1 to about 10, preferably from about 1 to about 8, more preferably from about 1 to about 6 and most preferably from about 1 to about 5 comprising:

(i) an ester wax; and (ii) a wax selected from the group consisting of diester waxes and triglyceride waxes and mixtures thereof.

Preferably, the ratio of (i) to (ii) ranges from about 10:1 to about 1:1, more preferably from about 5:1 to about 1:1 and most preferably from about 3:1 to about 1:1.

The HLB (short for "Hydrophile-Lipophile Balance") value system is fully described, and values for various materials are provided, in the publication *The HLB System, A Time-Saving Guide to Emulsifier Selection* (published by ICI Americas Inc., Wilmington, Del.; 1984), the disclosures of which are incorporated herein by reference in their entirety.

Useful ester waxes may include $C_{10}$-$C_{40}$ alcohols esterfied with $C_{10}$-$C_{40}$ fatty acid, diesters of $C_{10}$-$C_{40}$ fatty acid where the alcohol is propylene glycol, ethylene glycol, polyethylene glycol, polypropylene glycol, polyglycerin, or glycerin, triglycerides or diglycerides of $C_{10}$-$C_{40}$ fatty acid, pentaerythitol tri- or tetra-esters of $C_{10}$-$C_{40}$ fatty acids, $C_{10}$-$C_{40}$ fatty acids of sorbitan triesters, $C_{10}$-$C_{40}$ fatty acids of sucrose polyesters having 3–8 moles of substitution, myristyl myristate, paraffin, synthetic waxes such as Fischer-Tropsche waxes, microcrystalline waxes, castor wax, partially hydrogenated vegetable oils, behenyl behenrate and myristyl propionate and mixtures thereof.

Useful diester waxes may include Synchrowax ERL-C (available from Croda) and propylene glycol diester waxes including ethylene glycol distearate and glycol distearate. Useful triglyceride waxes include Shea Butter, Cocoa Butter, Synchrowax HGL-C, Synchrowax HRC, Synchrowax HRS-C (all available from Croda Inc.), tristearin, trimyristate and fully hydrogenated vegetable oils and mixtures thereof. Preferred is a mixture of diester and triglyceride waxes in a ratio of from about 5:1 to about 1:1 and more preferably from about 4:1 to about 1:1.

Waxes useful in the compositions of this invention are disclosed in the following, all of which are incorporated by reference herein in their entirety: U.S. Pat. No. 4,049,792, to Elsnau, issued Sep. 20, 1977; U.S. Pat. No. 4,151,272, to Geary et al., issued Apr. 24, 1975; U.S. Pat. No. 4,229,432, to Geria, issued Oct. 21, 1980; U.S. Pat. No. 4,280,994, to Turney, issued Jul. 28, 1981; U.S. Pat. No. 4,126,679, to Davy et al., issued Nov. 21, 1978; and European Patent Application Publication Number 117,070, to May, published Aug. 29, 1984, "The Chemistry and Technology of Waxes", A. H. Warth, 2nd Edition, reprinted in 1960, Reinhold Publishing Corporation, pp 391–393 and 421; "The Petroleum Chemicals Industry", R. F. Goldstein and A. L. Waddeam, 3rd Edition (1967), E & F.N. Span Ltd., pp 33–40; "The Chemistry and Manufacture of Cosmetics", M. G. DeNavarre, 2nd edition (1970), Van Nostrand & Company, pp 354–376; and in "Encyclopedia of Chemical Technology", Vol. 24, Kirk-Othmer, 3rd Edition (1979) pp 466–481.

(3) Emollients

The compositions of the present invention also preferably comprise at least one emollient. Preferred emollients are volatile silicone oils, non-volatile emollients, and the highly branched hydrocarbons known as the Permethyl 99 through 108A series (available from Permethyl Corporation) and mixtures thereof. The compositions of the present invention more preferably comprise at least one volatile silicone oil which functions as a liquid emollient, or especially in a mixture of volatile silicone oils and non-volatile emollients. The term "volatile", as used herein, refers to those materials which have a measurable vapor pressure at ambient temperature.

Volatile silicone oils useful in the compositions of the present invention are preferably cyclic. The following formula illustrates cyclic volatile polydimethylsiloxanes useful in the compositions disclosed herein:

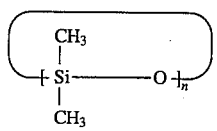

wherein n equals about 3 to about 7. Linear polydimethylsiloxanes contain from about 3 to about 9 silicon atoms per molecule and have the following general formula:

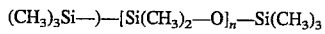

wherein n equals about 1 to about 7. Linear volatile silicone materials generally have viscosities of less than about 5 centistokes at 25° C. while cyclic materials typically have viscosities of less than about 10 centistokes. A description of various volatile silicone oils is found in Todd, et al., "Volatile Silicone Fluids for Cosmetics", *Cosmetics & Toiletries*, 91, pp. 27–32 (1976), the disclosures of which are incorporated by reference herein in their entirety.

Examples of preferred volatile silicone oils useful herein include: Dow Corning 344, Dow Corning 345, and Dow Corning 200 Series (manufactured by Dow Corning Corp.); Silicone 7207 and Silicone 7158 (manufactured by the Union Carbide Corp.); SF 1202 (manufactured by General Electric); and SWS-03314 (manufactured by SWS Silicones, Inc.).

The present compositions also preferably contain one or more non-volatile emollients. Such materials include fatty acid and fatty alcohol esters, such as cetyl alcohol and stearyl alcohol, hydrocarbons, non-volatile silicone oils, and mixtures thereof. Emollients among those useful herein are described in 1 *Cosmetics, Science and Technology* 27–104 (M. Balsam and E. Sagarin, Ed.; 1972), and U.S. Pat. No. 4,202,879, to Shelton, issued May 13, 1980 (both incorporated by reference herein).

Non-volatile silicone oils useful as an emollient material include polyalkylsiloxanes, polyalklyarylsiloxanes, and polyethersiloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C. Such polyalkyl siloxanes include the Vicasil series (sold by General Electric Company) and the Dow Corning 200 series (sold by Dow Corning Corporation). Polyalkylaryl siloxanes include polymethylphenyl siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company). Polysiloxane ethylene glycol ether copolymers are preferred copolymers for use in the present compositions.

Non-polar fatty acid and fatty alcohol esters useful herein as an emollient material include, for example, di-isopropyl adipate, isopropyl myristate, isopropyl palmitate, ethyl hexyl palmitate, propylene glycol myristyl ether acetate, isodecyl neopentanoate $C_{12}$-$C_{15}$ alcohol benzoate, diethyl hexyl maleate, PPG 14 butyl ether and PPG-2 myristyl ether propionate. Hydrocarbons such as isohexadecane (e.g., Permethyl 101A supplied by Presperse), petrolatum and USP light (e.g. Klearol®) or heavy (e.g. Kaydol®) mineral oils are also useful as emollients.

The emollients typically comprise in total from about 1% to about 50%, preferably from about 1% to about 25%, and more preferably from about 1% to about 10% by weight of the compositions of the present invention.

(4) Other Optional Carrier Materials

Other optional carrier materials include water, glycerin, alcohol (e.g., ethanol), coloring agents, polymer or film forming agents, perfuming agents, preservatives, and compatible pharmaceutical additives and actives (e.g., NSAI drugs; topical anesthetics such as benzocaine and lidocaine). Other optional carrier materials are agents selected to improve the cosmetic properties of the compositions, for example to reduce tackiness or stickiness.

The compositions of the present invention typically comprise, in total, from about 60% to about 99% pharmaceutically-acceptable sunscreen carrier material (which is typically one or more of the hereinbefore indicated materials), and preferably from about 80% to about 98%.

Methods for Providing Sun Protection

The present invention also relates to methods for providing photoprotection for humans or lower animals. Said methods comprise topically applying to the human or lower animal in need of photoprotection a safe and photoprotectively effective amount of compositions according to the present invention.

The following examples further describe and demonstrate embodiments within the scope of the present invention. These examples are given solely for the purpose of illustration, and are not to be construed as limitations of the present invention since many variations thereof are possible without departing from its spirit and scope.

EXAMPLE 1

An oil-in-water emulsion having an SPF above 8 is prepared by combining the following components utilizing a high sheer mixer (Greerco Corp., Gifford-Wood Model IL-79) and conventional mixing techniques.

| Components | Weight % |
|---|---|
| Water, purified | q.s. |
| Carbopol 1342 | 0.275 |
| Carbopol 934 | 0.275 |
| Allantoin | 0.200 |
| Disodium EDTA | 0.10 |
| Antifoam A Compound (simethicone) | 0.005 |
| Escalol 507 (octyldimethyl PABA) | 8.00 |
| Octyl Methoxy cinnamate | 5.50 |
| Spectrasorb UV-24 (benzophenone-8) | 0.50 |
| Spectrasorb UV-9 (oxybenzone) | 5.00 |
| Ganex V-220 (PVP/eicosene copolymer) | 2.00 |
| AC Copolymer 400 A (ethylene vinyl acetate copolymer) | 1.25 |
| Cetyl Alcohol | 1.00 |
| Stearyl Alcohol | 1.00 |
| Isodecyl Neopentanate | 2.00 |
| Propyl Paraben | 0.10 |
| Amphisol (DEA-cetyl phosphate) | 1.00 |
| Dimethicone | 1.00 |
| Propylene Glycol Myrsityl Ethyl Acetate | 1.00 |
| Aluminum Starch Octenyl Succinate | 1.00 |
| Dioctyl Maleate | 3.00 |
| Vitamin E Acetate | 0.50 |
| Triethanolamine 99% | 0.55 |
| Butylene Glycol | 2.00 |

| Components | Weight % |
| --- | --- |
| Methyl Paraben | 0.25 |
| Imidazolidinyl Urea | 0.30 |
| DMDM Hydantoin | 0.40 |
| Benzyl Alcohol | 0.50 |
| D,L-Panthenol | 0.50 |

EXAMPLE 2

An oil-in-water emulsion (creme) having an SPF above 8 is prepared by combining the following components using a high sheer mixer and conventional mixing techniques.

| Components | Weight % |
| --- | --- |
| Water, purified | q.s. |
| Carbopol 1342 | 0.15 |
| Carbopol 940 | 0.375 |
| Disodium EDTA | 0.10 |
| Antifoam A Compound (simethicone) | 0.05 |
| Allantoin | 0.20 |
| Butylene Glycol | 2.00 |
| Methyl Paraben | 0.25 |
| Escalol 507 (octyldimethyl PABA) | 8.00 |
| Octyl Methoxycinnamate | 5.50 |
| Spectrasorb UV-9 (oxybenzone) | 5.00 |
| $C_{12-15}$ Alcohols Benzoate | 3.00 |
| Ganex V-220 | 1.00 |
| AC Copolymer 400 A (ethylene vinyl acetate copolymer) | 1.25 |
| Dimethicone | 2.00 |
| Vitamine E Acetate | 0.50 |
| Propyl Paraben | 0.10 |
| Triethanolamine 99% | 0.525 |
| Imidazolidinyl Urea | 0.30 |
| DMDM Hydantoin | 0.40 |
| Benzyl Alcohol | 0.50 |
| DL-Panthenol | 0.50 |
| Fragrance | 0.15 |

EXAMPLE 3

Oil-in-water emulsion sprays having an SPF above 8 are prepared by combining the following components utilizing a high sheer mixer and conventional mixing techniques.

| Components | Weight % | Weight % |
| --- | --- | --- |
| Water, purified | q.s. | q.s. |
| Carbopol 1342 | 0.12 | 0.10 |
| Disodium EDTA | 0.10 | 0.10 |
| Antifoam A (simethicone) | 0.01 | 0.005 |
| Allantoin | 0.20 | 0.20 |
| Methyl Paraben | 0.25 | 0.25 |
| Triethanolamine 99% | 0.37 | 0.10 |
| Octocrylene | 5.00 | 5.00 |
| Menthyl Anthranilate | 5.00 | 5.00 |
| Octyl Methoxycinnamate | 7.50 | 7.50 |
| Octyl Salicylate | 5.00 | 5.00 |
| Ganex V-220 (PVP/eicosene copolymer) | 1.00 | 1.00 |
| Vitamin E Acetate (d-alpha) | 0.50 | 0.50 |
| AC Copolymer 400 A (Ethylene Vinyl Acetate Copolymer) | 0.50 | 0.50 |
| Silicone Copolymer L-755 | 0.50 | 0.50 |
| Propyl Paraben | 0.10 | 0.10 |
| Stearic Acid | 0.50 | — |
| Imidazolidinyl Urea | 0.30 | 0.30 |
| DMDM Hydantoin | 0.40 | 0.40 |
| d-Pantothenol | 0.50 | 0.50 |
| $C_{12-15}$ Alcohols Benzoate | — | 2.00 |
| Dimethicone | — | 1.00 |
| Fragrance | 0.25 | 0.25 |
| Sodium Chloride | — | 0.001 |

EXAMPLE 4

An oil-in-water emulsion (lotion) having an SPF above 8 is prepared by combining the following components utilizing a high sheer mixer (Tekmar, Model RW20DZM) and conventional mixing techniques.

| Components | Weight % |
| --- | --- |
| Octocrylene | 5.000 |
| Octyl Methoxycinnamate | 7.500 |
| Octyl Salicylate | 5.000 |
| Menthyl Anthranilate | 5.000 |
| Distilled Water | q.s. |
| Disodium EDTA | 0.050 |
| Glycerin | 2.000 |
| Methyl Paraben | 0.250 |
| Propyl Paraben | 0.150 |
| Butylated Hydroxyanisole | 0.050 |
| Imidazolidinyl Urea | 0.300 |
| Butylene Glycol | 2.000 |
| Carbomer 954 | 0.150 |
| Acrylic Acid Copolymer | 0.100 |
| Triethanolamine | 0.310 |
| DEA Cetyl Phosphate | 0.200 |
| Cetyl Palmitate | 0.750 |
| Isoarachidyl Neopentanoate | 2.000 |
| Glycerol Tribehenate | 0.750 |
| Stearoxytrimethylsilane (and) Stearyl Alcohol | 0.500 |
| PVP Eicosene Copolymer | 1.250 |
| Stearic Acid | 0.050 |
| PEG 10 Soya Sterol | 0.050 |
| Aluminum Starch Octenyl succinate | 0.500 |
| Allantoin | 0.200 |
| DL-Panthenol | 0.500 |
| Vitamin E Acetate | 0.500 |

EXAMPLE 5

An oil-in-water emulsion (lotion) having an SPF above 8 is prepared by combining the following components utilizing a high sheer mixer and conventional mixing techniques.

| Components | Weight % |
| --- | --- |
| Ethyl Hexyl p-methoxycinnamate | 7.500 |
| Octocrylene | 5.000 |
| Octyl Salicylate | 5.000 |
| Menthyl Anthranilate | 5.000 |
| Water, purified | q.s. |
| Isoarchidyl Neopentanoate | 2.000 |
| PVP Eicosene Copolymer | 2.500 |
| Butylene Glycol | 2.000 |
| Dimethicone | 1.500 |
| Cetyl Phosphate and DEA Cetyl Phosphate | 1.500 |
| Cetyl Alcohol | 1.250 |
| Stearyl Alcohol | 1.250 |
| Benzyl Alcohol | 0.500 |
| DMDM Hydantoin | 0.400 |
| Imidazolidinyl Urea | 0.300 |
| Methyl Paraben | 0.250 |
| Acrylic Acid Copolymer | 0.150 |
| Triethanolamine | 0.150 |
| Propyl Paraben | 0.125 |
| Disodium EDTA | 0.100 |

-continued

| Components | Weight % |
| --- | --- |
| Allantoin | 0.200 |
| DL-Panthenol | 0.500 |
| Vitamin E Acetate | 0.500 |

EXAMPLE 6

An oil-in-water emulsion (creme) having an SPF above 8 is prepared by combining the following components using a high sheer mixer and conventional mixing techniques.

| Components | Weight % |
| --- | --- |
| Octocrylene | 5.00 |
| Octyl Salicylate | 5.000 |
| PVP Eicosene Copolymer | 2.000 |
| Ethylene/Vinyl Acetate Copolymer | 1.250 |
| Acrylic Acid Copolymer | 0.275 |
| Carbomer | 0.275 |
| Water | q.s. |
| Triethanolamine | 0.550 |
| Cetyl Alcohol | 1.000 |
| Stearyl Alcohol | 1.000 |
| Allantoin | 0.200 |
| Simethicone | 0.005 |
| DL-Panthenol | 0.500 |
| Butylene Glycol | 2.000 |
| Methyl Paraben | 0.250 |
| Propyl Paraben | 0.100 |
| DMDM Hydantoin | 0.400 |
| Imidazolidinyl Urea | 0.300 |
| Disodium EDTA | 0.100 |
| Benzyl Alcohol | 0.500 |
| Cetyl Phosphate (and) DEA Cetyl Phosphate | 1.000 |
| Dimethicone | 1.000 |
| Ethylhexyl p-methoxy cinnamate | 7.500 |
| Aluminum Starch Octenylsuccinate | 1.000 |
| Vitamin E Acetate | 0.500 |
| Isoarachidlyl Neopentanoate | 2.000 |
| Menthyl Anthranilate | 5.00 |

What is claimed:

1. A sunscreen composition having enhanced photoprotective effect comprising:

(a) from about 0.1% to about 2% allantoin;

(b) from about 0.1% to about 5% panthenol;

(c) from about 0.1% to about 5% Vitamin E, Vitamin E acetate, or mixtures thereof;

(d) from about 1% to about 30% of one or more sunscreen agents; and (e) from about 60% to about 99% of a pharmaceutically-acceptable sunscreen carrier material;

and wherein further said sunscreen composition has an SPF value of about 8 or greater.

2. A sunscreen composition according to claim 1 wherein said sunscreen agents are selected from the group consisting of 2-ethylhexyl p-methoxycinnamate, butylmethoxydibenzoylmethane, 2-hydroxy-4-methoxybenzophenone, octyldimethyl p-aminobenzoic acid, 2,2'-dihydroxy-4-methoxybenzophenone, octocrylene, menthyl anthranilate, titanium dioxide, and ethyl hexyl salicylate, and mixtures thereof.

3. A sunscreen composition according to claim 1 wherein said sunscreen agents are selected from the group consisting of 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N(2-ethylhexyl)methylaminobenzoic acid ester with 4-hydroxydibenzoylmethane; 4-N,N-(2-ethylhexyl)methylaminobenzoic acid ester of 2-hydroxy-4-(2-hydroxyethoxy)benzophenone; 4-N,N-(2-ethylhexyl)methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)4-aminobenzoic acid ester of 4-(2-hydroxyethoxy)dibenzoylmethane; and mixtures thereof.

4. A sunscreen composition having enhanced photoprotective effect comprising:

(a) from about 0.1% to about 1% allantoin;

(b) from about 0.1% to about 3% panthenol;

(c) from about 0.1% to about 3% Vitamin E, Vitamin E acetate, or mixtures thereof;

(d) from about 1% to about 30% of one or more sunscreen agents; and (e) from about 60% to about 99% of a pharmaceutically-acceptable sunscreen carrier material;

and wherein further said sunscreen composition has an SPF value of about 15 or greater.

5. A sunscreen composition according to claim 4 wherein said sunscreen agents are selected from the group consisting of 2-ethylhexyl p-methoxycinnamate, butylmethoxydibenzoylmethane, 2-hydroxy-4-methoxybenzophenone, octyldimethyl p-aminobenzoic acid, 2,2'-dihydroxy-4-methoxybenzophenone, octocrylene, menthyl anthranilate, titanium dioxide, and ethyl hexyl salicylate, and mixtures thereof.

6. A sunscreen compositions according to claim 4 wherein said sunscreen agents are selected from the group consisting of 4-N,N- (2-ethyl hexyl)methyl aminobenzoic acid ester of 2,4-dihydroxybenzophenone; N,N-di-(2-ethylhexyl)-4-aminobenzoic acid ester with 4-hydroxydibenzoylmethane; 4-N,N(2-ethylhexyl) methylaminobenzoic acid ester with 4-hydroxydibenzoylmethane; 4-N,N-(2-ethylhexyl)methylaminobenzoic acid ester of 2-hydroxy-4-(2-hydroxyethoxy)benzophenone; 4-N,N-(2-ethylhexyl) methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)4-aminobenzoic acid ester of 4-(2-hydroxyethoxy)dibenzoylmethane; and mixtures thereof.

7. A sunscreen composition having enhanced photoprotective effect comprising:

(a) from about 0.1% to about 5% allantoin;

(b) from about 0.1% to about 1% DL-panthenol;

(c) from about 0.1% to about 3% Vitamin E, Vitamin E acetate, or mixtures thereof;

(d) from about 2% to about 20% of one or more sunscreen agents selected from the group consisting of 2-ethylhexyl p-methoxycinnamate; butylmethoxydibenzoylmethane; 2-hydroxy-4-methoxybenzophenone; octyldimethyl p-aminobenzoic acid; 2,2'-dihydroxy-4-methoxbenzophenone; octocrylene; octyl salicylate; menthyl anthranilate; titanium dioxide; ethyl hexyl salicylate; 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N(2-ethylhexyl) methylaminobenzoic acid ester with 4-hydroxydibenzoylmethane; 4-N,N-(2-ethylhexyl)methylaminobenzoic acid ester of 2-hydroxy-4-(2-hydroxyethoxy)benzophenone; 4-N,N-(2-ethylhexyl) methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)4-aminobenzoic acid ester of 4-(2-hydroxyethoxy)dibenozylmethane; and mixtures thereof; and (e) from about 80% to about 98% of a pharmaceutically-acceptable sunscreen carrier material;

and wherein further said sunscreen composition has an SPF value of about 20 or greater.

8. A method for providing photoprotection, said methods comprising topically applying to a human or lower animal in need of photoprotection a safe and photoprotectively effective amount of a sunscreen composition according to claim 1.

9. A method for providing photoprotection, said methods comprising topically applying to a human or lower animal in need of photoprotection a safe and photoprotectively effective amount of a sunscreen composition according to claim 2.

10. A method for providing photoprotection, said methods comprising topically applying to a human or lower animal in need of photoprotection a safe and photoprotectively effective amount of a sunscreen composition according to claim 3.

11. A method for providing photoprotection, said methods comprising topically applying to a human or lower animal in need of photoprotection a safe and photoprotectively effective amount of a sunscreen composition according to claim 4.

12. A method for providing photoprotection, said methods comprising topically applying to a human or lower animal in need of photoprotection a safe and photoprotectively effective amount of a sunscreen composition according to claim 5.

13. A method for providing photoprotection, said methods comprising topically applying to a human or lower animal in need of photoprotection a safe and photoprotectively effective amount of a sunscreen composition according to claim 6.

14. A method for providing photoprotection, said methods comprising topically applying to a human or lower animal in need of photoprotection a safe and photoprotectively effective amount of a sunscreen composition according to claim 7.

* * * * *

UNITED STATES PATENT AND TRADEMARK OFFICE
CERTIFICATE OF CORRECTION

PATENT NO. : 5,573,754

DATED : November 12, 1996

INVENTOR(S) : Rupali A. Kulkarni and George E. Deckner

It is certified that error appears in the above-identified patent and that said Letters Patent is hereby corrected as shown below:

At column 5, line 20 "3,3,,5" should read --3,3,5--.

At column 5, line 29 "butyl methoxydibenzoylmethane" should read --butylmethoxydibenzoylmethane--.

At column 9, line 12 "$(CH_3)_3Si$-)-$[Si(CH_3)_2$-$O]_n$-$Si(CH_3)_3$" should read --$(CH_3)_3Si$-$O$-$[Si(CH_3)_2$-$O]_n$-$Si(CH_3)_3$--.

At column 10, line 62 "Myrsityl Ethyl" should read --Myristyl Ether--.

At column 12, lines 36-37 "Octenyl succinate" should read --Octenylsuccinate--.

At column 12, line 54 "Isoarchidyl" should read --Isoarachidyl--.

At column 13, line 37 "Isoarachidlyl" should read --Isoarachidyl--.

At column 14, line 16 please move subpoint (e) to the beginning of line 17.

At column 14, line 29 "compositions" should read --composition--.

At column 14, line 31 "methyl aminobenzoic" should read --methylaminobenzoic--.

Signed and Sealed this

Eighteenth Day of March, 1997

*Attest:*

BRUCE LEHMAN

*Attesting Officer*  Commissioner of Patents and Trademarks